(12) United States Patent
Tydings

(10) Patent No.: US 6,805,837 B2
(45) Date of Patent: Oct. 19, 2004

(54) ASSAYING DEVICE AND METHOD FOR IN FIELD URINALYSIS

(76) Inventor: Barry M. Tydings, 1661 Devonshire Ct., Westlake Village, CA (US) 91361

( * ) Notice: Subject to any disclaimer, the term of this patent is extended or adjusted under 35 U.S.C. 154(b) by 11 days.

(21) Appl. No.: 10/264,605

(22) Filed: Oct. 4, 2002

(65) Prior Publication Data

US 2003/0165405 A1 Sep. 4, 2003

Related U.S. Application Data

(63) Continuation of application No. 10/091,162, filed on Mar. 4, 2002, now Pat. No. 6,497,843.

(51) Int. Cl.$^7$ .............................................. G01N 21/00
(52) U.S. Cl. ............................ 422/58; 422/60; 422/50; 422/56; 422/61; 422/102; 436/164; 436/169
(58) Field of Search ............................... 422/58, 50, 60, 422/56, 61, 102, 55, 57, 68.1, 99, 100; 436/164, 169

(56) References Cited

U.S. PATENT DOCUMENTS

| | | | |
|---|---|---|---|
| 3,849,256 A | * | 11/1974 | Linder ..................... 435/287.7 |
| 4,624,929 A | | 11/1986 | Ullman |
| 5,119,830 A | | 6/1992 | Davis |
| 5,186,897 A | | 2/1993 | Eason et al. |
| 5,403,551 A | | 4/1995 | Galloway et al. |
| 5,409,664 A | | 4/1995 | Allen |
| 5,523,055 A | | 6/1996 | Hansen et al. |
| 5,605,161 A | | 2/1997 | Cross |
| 5,618,494 A | | 4/1997 | Bunce et al. |
| 5,656,502 A | | 8/1997 | MacKay et al. |
| 5,770,458 A | * | 6/1998 | Klimov et al. .............. 436/518 |
| 6,368,873 B1 | | 4/2002 | Chang et al. |
| 6,379,620 B1 | | 4/2002 | Tydings et al. |
| 6,379,620 C1 | | 8/2002 | Tydings et al. |
| 6,497,843 B2 | | 12/2002 | Tydings |
| 6,514,769 B2 | | 2/2003 | Lee |
| 6,548,019 B1 | | 4/2003 | Lee et al. |

FOREIGN PATENT DOCUMENTS

| | | |
|---|---|---|
| EP | 0 333 286 | 9/1989 |
| WO | WO 00/2911 | 5/2000 |

OTHER PUBLICATIONS

Syntron Bioresearch Inc., Dip DrugScan 6 Test, Instructions, pp. 1–4).

* cited by examiner

Primary Examiner—Jill Warden
Assistant Examiner—Sam P. Siefke
(74) Attorney, Agent, or Firm—Greenberg Traurig LLP; Charles Berman, Esq.; Claude Nassif

(57) ABSTRACT

An assay device for in field urine analysis including a container having an opening for collecting a urine sample, a cover for sealing the opening of the container and an assay assembly provided in the container for chemically analyzing the urine sample. The assay assembly comprises a liquid impermeable backing, a wicking material provided on a rear surface of the backing, at least one assay strip provided on a front surface of the backing and adjacent a top edge of the backing in contact with the wicking material, a front cover provided on the front surface of the backing for sealing the assay strip to the backing at a bottom and two sides of the assay strip and a rear cover provided on the rear surface of the backing for together with the front cover sealing said wicking material and the assay strip adjacent the top edge and two sides of said wicking material.

30 Claims, 2 Drawing Sheets

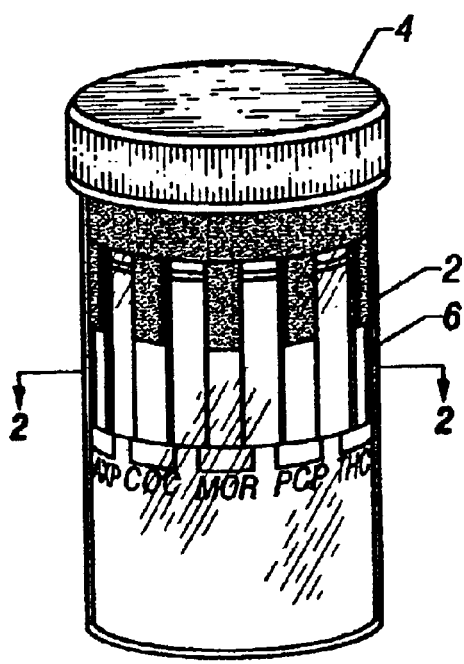
FIG. 1
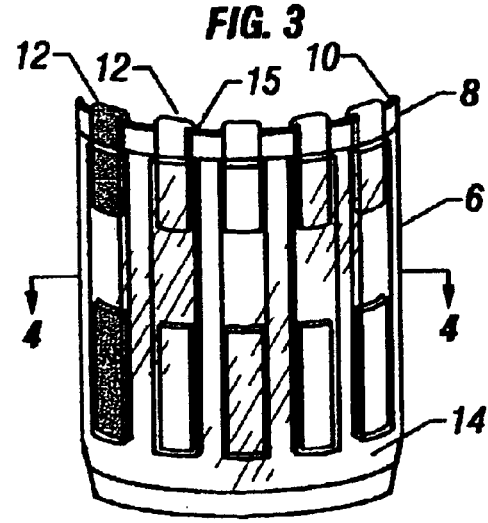
FIG. 3
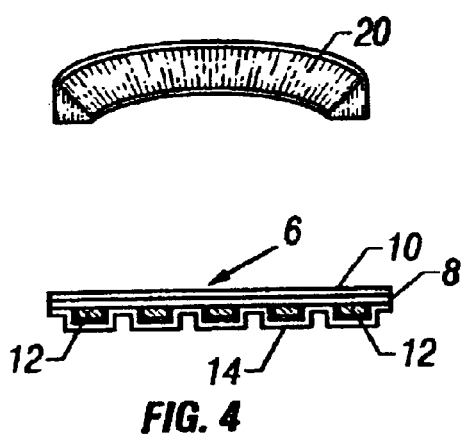
FIG. 5
FIG. 4
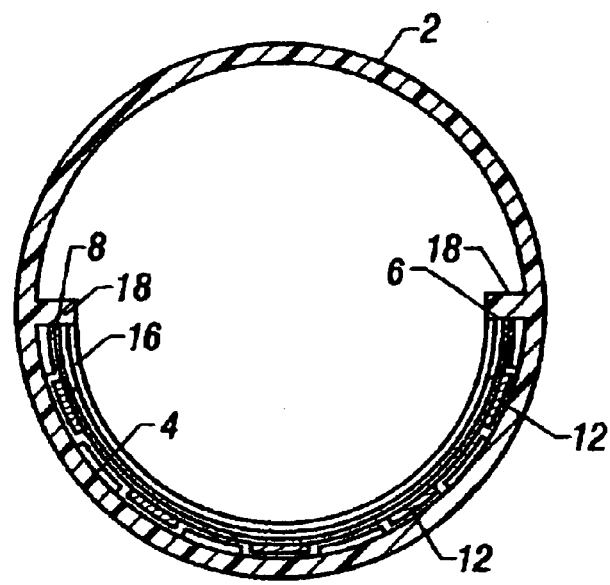
FIG. 2

ASSAYING DEVICE AND METHOD FOR IN FIELD URINALYSIS

This application is a Continuation of application Ser. No. 10/091,162, filed Mar. 4, 2002 now U.S. Pat. No. 6,497,843, which application is incorporated herein by reference.

BACKGROUND OF THE INVENTION

1. Field of the Invention

This invention relates to assaying devices and particularly to assaying devices suitable for use in the field for determining the presence of undesirable chemical constituents or diseases.

2. Prior Art

With the increasing availability and use of drugs by the general population, employers such as government agencies, sports groups and transportation related companies utilize drug screenings as both conditions of employment and maintenance of safety in the workplace. To have a doctor present at the workplace to perform the drug screenings is both expensive and impractical for an employer. Accordingly, other methods have been developed to perform the drug screenings.

One such prior art method is shown in U.S. Pat. No. 5,403,551 entitled Assaying Device and Container for In Field Analysis of a Specimen and Later Shipment of the Unadulterated Specimen.≅ This device is supposed to be designed to be utilized in field by laymen; however, it is relatively expensive to manufacture because it requires special components, and particularly a special cup, and is relatively complex to operate by laymen and is subject to leakage and contamination.

SUMMARY OF THE INVENTION

Accordingly, it is a general object of the present invention to provide an assaying device which overcomes the disadvantages of the prior art.

In particular, it is a general object of the present invention to provide an assaying device which is capable of easily collecting and testing a urine sample while maintaining the urine sample unadulterated and secure.

It is still another object of the present invention to provide an assaying device which can be used in the field which is simple to use and inexpensive and easy to manufacture.

In keeping with the principles of the present invention, the objects are accomplished by an assaying device for in field urine analysis which includes a container having an opening for collecting a urine sample, a cover for sealing the opening of the container and an assay assembly provided in the container for chemically analyzing the urine sample. The assay assembly includes a liquid impermeable backing, a wicking means provided on a rear surface of said backing, at least one assay strip provided on a front side of the backing and extending over a top edge of the backing and overlaying the wicking material, a front cover provided on the front side of the backing for sealing the assay strip to the backing at the bottom and two sides of the assay strip and a rear cover provided on the rear of the backing for together with the front cover sealing the wicking material and the overlaying assay strip at a top and two sides of the wicking material.

BRIEF DESCRIPTION OF THE DRAWINGS

The above-mentioned features and objects of the present invention will become more apparent with reference to the following description taken in conjunction with the accompanying drawings wherein like reference numerals denote like elements and in which:

FIG. 1 is a side view of an assay device in accordance with the teachings of the present invention;

FIG. 2 is a cross-sectional view of a first embodiment of an assay device in accordance with the teachings of the present invention taken along the lines 2—2 in FIG. 1;

FIG. 3 is a front view of a first embodiment of an assay means in accordance with the teachings of the present invention;

FIG. 4 is a cross-section of FIG. 3 along the lines 4—4 of FIG. 3;

FIG. 5 is a view of a partial retaining ring utilized in a first embodiment of an assay device in accordance with the teachings of the present invention;

DETAILED DESCRIPTION OF THE INVENTION

Figure 6:
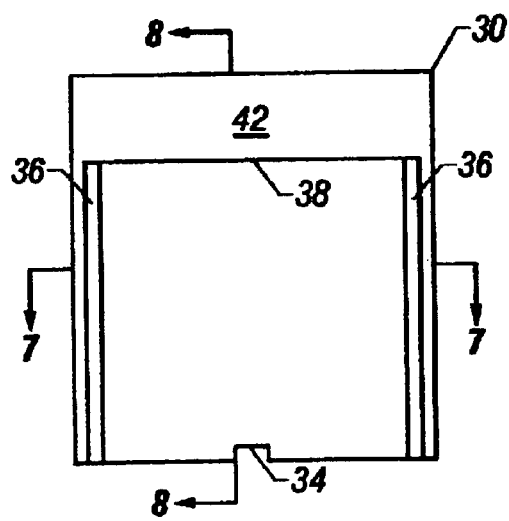
FIG. 6 is a front view of a portion of an assay means in accordance with a second embodiment of the present invention.
Figure 7:
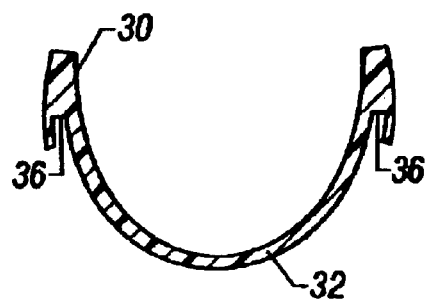
FIG. 7 is a cross-sectional view of FIG. 6 along the lines 7—7 in FIG. 6.
Figure 8:
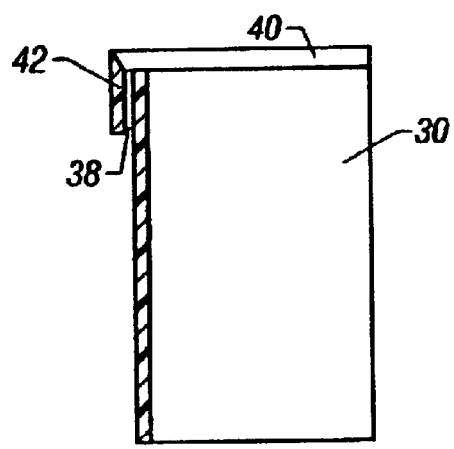
FIG. 8 is a cross-sectional view of FIG. 6 along the lines 8—8 in FIG. 6.

Referring to FIGS. 1–5, shown therein is a first embodiment of an assay device in accordance with the teachings of the present invention. The assay device generally includes a container 2 with a screw lid 4 for closing the open end of the container 2. Inside of the container 2 is provided an assay means 6 such as is shown in FIG. 3. The assay means 6 is installed within the container 2 as is shown in FIG. 2.

In particular, the assay device 6 comprises a backing 8 which is made from a resilient, liquid impermeable material. Typically one such material would be a plastic which is not reactive with any of the components of urine. On the rear side of the backing 8 is provided a wicking material 10. The wicking material 10 extends substantially the full length of the backing 8 and can be made of any material which will wick up a liquid such as filter paper, unwoven papers, fiber glass, etc.

Assay strips 12 are provided on a front surface of the backing 8. These assay strips 12 are for the purpose of chemically analyzing the urine sample to see if it contains any drugs such as amphetamines, cocaine, morphine, PCP, THC and/or their metabolites. To test for these drugs, the assay strips 12 each contain a reagent which is well known in the art for detecting an appropriate drug. Such reagents include, but are not limited to, colloidal gold coated sheep polyclonal anti-amphetamine, mouse monoclonal anti-benzoyl ecgonine, polyclonal rabbit anti-morphine-3 glucuronide, mouse monoclonal anti-cannabinoid or mouse monoclonal anti-phencyclidine, appropriate drug or drug analog conjugates, and immobilized antisera.

The front surface of the backing 8 is covered by a front cover 14 which seals the assay strips 12 at the bottom and both sides of each assay strips 12 so as to isolate each assay strip 12 from each other and prevent contamination from either the urine or another assay strip 12. The front cover 14 is sealed to the backing 8 by a suitable adhesive or other means such as ultrasonic or heat welding. The top portion of the reagent strip 12 is bent over the top edge 15 of the backing 8 and overlapped onto the wicking paper 10. Alternatively, the wicking material 10 can be folded over the top edge 15 and overlapped onto the assay strips 12. The assay device 6 together with a rear cover 16 are inserted into the container 2 as shown in FIG. 2. The container 2 is provided with longitudinally extending tabs 18 which help hold the assay means 6 in place in the container 2. A partial snap ring 20 as shown in FIG. 5 is then inserted into the container 2 above the assay means 6 and between the tabs 18 to hold the assay means 6 in place and to prevent urine from entering the assay means from the top.

In actual construction, the assay means 6 is substantially the same height in the longitudinal direction as the container 2 with the rear cover 16 being slightly shorter so as to leave a small gap between the bottom of the container 2 and the bottom end of the rear cover 16. Also, it is preferred that the container 2 and front cover 14 be made from transparent plastic.

In operation, the cap 4 is unscrewed from the container 2. A urine sample is then introduced into the container 2. The urine sample need only by minimum in volume and only needs to be deep enough to cover the gap between the bottom of the container 2 and the bottom end of the rear cover 16. As soon as the urine sample is introduced, the cap 4 should be tightly screwed onto the container 2 to prevent any contamination of the urine sample. The urine then wicks up the wicking material 10 until it reaches the overlapped portions of the assay strips 12. The urine then wicks over the top edge of the backing 8 and down the assay strips 12. The urine wicking down the assay strips 12 will react with the chemical agents contained therein and will give positive, negative or inconclusive test results. If the results are positive, the container can then be sealed with an evidence tape and sent to a certified laboratory for confirmation of the in field test results without contaminating or adulterating the urine sample contained within the container 2.

Figure 9:
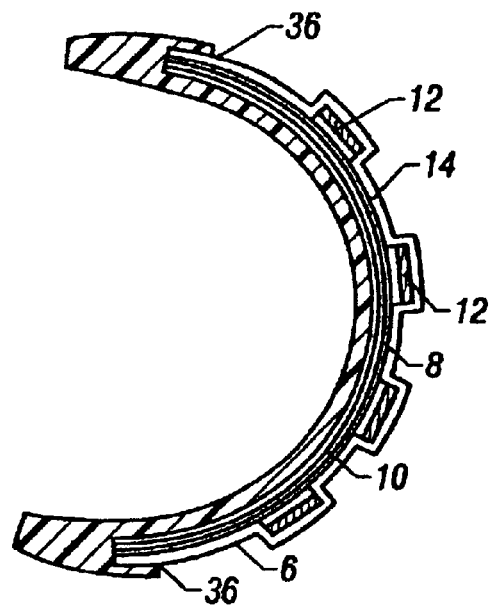
FIG. 9 is a cross-sectional view similar to that of FIG. 2 illustrating a completed assay assembly in accordance with a second embodiment of the present invention ready for installation into the container of the assay device.

Referring to FIGS. 6, 7, 8, and 9, shown therein is a second embodiment of the assay device of the present invention. In particular, shown in the FIGS. 6–9 is essentially an injection molded rear cover 30 for holding the assay means 6 comprising the front cover 14, backing 8, wicking material 10 and assay strips 12. The injection molded rear cover 30 is substantially the same height as the inside of the container 2, is injection molded from a suitable resilient plastic and is provided at the bottom of the front of the curved portion 32 with a cut-out 34. Both sides of the curved portion 32 are further provided with vertically extending slots 36 and a horizontally extending slot 38 as is shown in the FIGS. 7 and 8. The inside top portion of the injection molded rear cover 30 is provided with a beveled edge 40 to assist in the guiding of the urine sample into the inside of the container 2 and further prevent contamination of the assay means 6. As can be seen in FIG. 9, the assay means 6 is assembled to the injection molded rear cover 30 by means of inserting it into the vertical slots 36 and horizontal slot 38. This assembled piece is then placed inside of the container 2 and the cap 4 screwed thereon. In some constructions, it may be desirable to first apply a suitable adhesive to a portion of the upper horizontally extending surface 42 of the rear cover 30. Also, to reduce the cost of manufacture, a container without tabs 18 can be used.

The operation of this second embodiment is substantially the same as the first. In particular, the cap 4 is first removed from the container 2. A urine sample is then provided into the container 2 and the cap 4 is screwed back onto the container 2. The urine sample propagates through the slot 34 and wicks up through the wicking material 10 until it reaches the assay strips 12. The urine sample then wicks over the top of the backing 8 and down the assay strips 12 to activate the various chemical reagents to test for various drugs.

It should also be apparent that while the present invention has been described in terms of testing for drugs, it could be modified by utilizing other reagents and chemicals on the assay strips to test for anything which might be present in the urine. It could be utilized to test for sugar, uric acid, ammonia, alcohol and other sexually transmitted diseases such as clomedia. It should be apparent to those skilled in the art that the above-described embodiments are merely illustrative of but a few of the embodiments which could be created by one of ordinary skill in the art without departing from the spirit and scope of the present invention.

We claim:

1. An assaying device for in field urine analysis comprising:
   a container having an opening for collecting a urine sample, a base for the container, and a wall for the container,
   a cover for sealing the opening of the container;
   an assay assembly with the container for chemically analyzing the urine sample, the assay assembly having at least one assay strip provided for the assembly and being in liquid transmittable contact with wicking, the wicking having a lower portion proximal to the base of the container and being for communication with urine in the container such that, in use, when there is urine in the container and the container is in an upright position with the opening above the base, the urine wicks up the wicking to the assay strip thereby to permit a flow of urine in the container to the assay strip; and
   the assay strip being directed adjacent to the wall of the container thereby to be readable through the container wall.

2. A device as claimed in 1, wherein the layer includes slots spaced apart in the front face of the layer, the slots being directed longitudinally and being for accommodating sides of an assay strip in adjacency with a front surface of the layer and in adjacency to a wall of the container.

3. A device as claimed in claim 2 including a transverse slot extending between the longitudinal slots and being in communication between slots for accommodating an end of the assay strips.

4. An assaying device as claimed in claim 1, including a series of assay strips in parallel relationship on the assay assembly.

5. An assaying device as claimed in claim 1, wherein the wicking material acts to draw urine upwardly to the assay strip.

6. An assaying device as claimed in claim 1, wherein the assay assembly is substantially the same height as the height of the container.

7. An assaying device as claimed in claim 1, wherein the assay assembly conforms to the inner wall of the container.

8. An assaying device as claimed in claim 1, wherein the container includes and an essentially circular portion for receiving a screw-on cap to close the circular portion.

9. An assay assembly for chemically analyzing a urine sample in a container, the assay assembly comprising:
   a backing;
   at least one assay strip provided on a front surface of the backing so that, in use, it is arranged for being in liquid transmittable contact with urine in the container so that urine in the container travels to the assay strip;

a front cover provided on the front surface of the backing to facilitate locating the assay strip between the backing and the front cover;

the backing together with the front cover and the assay strip being locatable adjacent a wall of a container and extendable from a position proximal to the bottom of the container to a position proximal to the top of the container; and a wicking element extending from the front of the backing to the back of the backing to facilitate urine flow from the container to the assay strip.

10. An assembly according to claim 9, including a rear cover for supporting the backing, assay strip and front cover, the rear cover conforming at least in part to the container wall.

11. An assaying assembly as claimed in claim 9, wherein the wicking material acts to draw urine upwardly.

12. An assaying device as claimed in claim 9, wherein the container has a curved wall profile.

13. An assaying device as claimed in claim 9 wherein the container has a curved wall profile, and the assay assembly is for adjacency with the curved wall.

14. An assay assembly for chemically analyzing a urine sample, the assay assembly comprising:

a container with an opening and a base;

a liquid impermeable backing;

at least one assay strip provided on a front surface of the liquid impermeable backing;

a wicking provided with one portion of the wicking being in fluid connection to the assay strip with another portion of the wicking being for contact with a urine sample in the container for receiving the assembly and having a lower portion proximal to the base of the container so that, in use, when urine is in the container and the container is in an upright position with the opening above the base, urine wicks up to the assay strip and thereby permits a flow of urine in the container to the assay strip;

a front cover provided on the front surface of the liquid impermeable backing for locating the assay strip between the front cover and the liquid impermeable backing; and the assembly being for mounting against a wall of a container thereby to be visible through the container wall.

15. An assaying device for in field urinalysis comprising:

a substantially transparent container having an opening for collecting a urine sample and a base for the container;

a cover for sealing the opening of the container;

an assay assembly provided in the container for chemically analyzing the urine sample, the assay assembly comprising a liquid impermeable layer, at least one assay strip provided on a front surface of the liquid impermeable layer facing outwardly and being viewable through the container;

at least one wicking, the wicking having a lower portion proximal to the base of the container and being an intermediate element extending to the assay strip and being arranged with one portion of the intermediate wicking extending to communicate with the assay strip to permit urine to pass from the wicking to the assay strip; and an element provided to the assay assembly for inhibiting the assay strip from liquid contact with the urine sample except through the wicking so that, in use, urine wicks through the wicking to the strip, and up the strip when the container is located with the opening above the base.

16. An assaying device for in field urine analysis, comprising:

a substantially transparent container having an opening for collecting a urine sample, and a base for the container;

a cover for sealing the opening of the container and the container being operable when in an upright position to effect the assaying;

an assembly including a rear surface for supporting a liquid impermeable backing for mounting a liquid impermeable backing for an assay assembly in the container, the rear surface being shaped to conform generally to the container wall, and to extend at least partly in adjacency with the periphery of the container, the assay assembly having the liquid impermeable layer, at least one assay strip provided on a front surface of the liquid impermeable layer facing outwardly and viewable through the container; and at least one wicking for contacting the assay strip at one end of the wicking and for contacting the urine at the other end of the wicking, and having a lower portion proximal to the base of the container, and for causing urine to wick to the assay strip, and up the strip when the container is located with the opening above the base.

17. A device according to claim 16, wherein the rear surface of the assembly is injection molded and made from a flexible resilient material, and includes a pair of slots spaced apart in the front face of the support, the slots being directed longitudinally and being for accommodating the sides of the assay strip in adjacency with a surface of the support and in adjacency to a wall of the container, and including a transverse slot extending between the longitudinal slots and being in communication between the slots for accommodating the assay strip.

18. A method for in field urine analysis in an assay device, the device comprising:

a substantially transparent container having an opening for collecting a urine sample, and a base for the container;

a cover for sealing the opening of the container; and an assay assembly provided for the container for chemically analyzing the urine sample, the assay assembly comprising a liquid impermeable backing, at least one assay strip provided on a front surface of the backing to face outwardly and be viewable through the container, a front cover provided on the front surface of the backing, and the front cover locating be assay strip between the front cover and the backing; and the method including the steps of:

introducing a urine sample into the container;

locating the container with the opening above the base, and the wicking having a portion extending for connection with a urine sample in the container and a portion for adjacency with the assay strip;

allowing urine to wick up a wicking to the assay strip; and analyzing the urine on the assay strip.

19. A method as claimed in claim 18 wherein the urine wicks solely up the wicking until it reaches the assay strip thereby to provide for continuous flow of the urine to the assay strip.

20. A method as claimed in claim 18 including extending the wicking from the front end of the backing to the rear end of the backing, and wherein the urine wicks both down and up the wicking in traveling from the container to the assay strip thereby to provide for continuous flow of urine to the assay strip.

21. A device as claimed in claim 1 wherein the assay is performed without inverting the container.

22. An assembly as claimed in claim 9 wherein the assay is performed without inverting the container.

23. An assembly as claimed in claim 14 wherein the assay is performed without inverting the container.

24. An assembly as claimed in claim 15 wherein the assay is performed without inverting the container.

25. A device as claimed in claim 16 wherein the assay is performed without inverting the container.

26. A method as claimed in claim 18 wherein the assay is performed without inverting the container.

27. An assaying device comprising:

a container having a base, an opening and a top for closing the opening;

a wicking having a lower portion proximal to the base of the container and an upper portion removed from the base in the direction of the opening of the container;

at least one assay strip contacting the wicking in proximity of the removed portion of the wicking, and the wicking having a lower portion proximal to the base of the container, to allow analysis of a urine sample through contact of the urine with the one assay strip; and wherein, in use the urine contacts the assay strip during transmission of the urine from the lower portion of the wicking to the upper portion of the wicking.

28. An assaying device comprising:

a container having a base, an opening end a top for closing the opening;

a wicking having a lower portion proximal to the base and an upper portion proximal to the opening of the container;

at least one assay strip contacting the wicking in proximity of the upper position of the wicking, and the wicking having a lower portion proximal to the base of the container, to allow analysis of a urine sample through contact of the urine with the assay strip; and wherein, a path of the urine to the strip has a first portion where the urine moves, along the wicking, in a direction from the base towards the opening of the container, and a second portion where the urine reaches the assay strip and moves along the assay strip in the direction from the base towards the opening of the container.

29. An assaying device comprising:

a container having a base, an opening and a top for closing the opening;

a wicking having a lower portion proximal to the base of the container and an upper portion proximal to the opening of the container;

at least one assay snip contacting the wicking in proximity of the upper portion of the wicking, and the wicking having a lower portion proximal to the base of the container, to allow analysis of a urine sample through contact of the urine with the assay strip; and wherein, in use, the urine contacts the assay strip while moving along the wicking in an upward direction, the upward direction being defined by a direction from the base towards the opening.

30. An assaying device comprising:

a container having a base, an opening and a top for closing the opening;

a wicking having a lower portion proximal to the base of the contain and an upper portion proximal to the opening of the container;

at least one assay strip contacting the wicking in proximity of the upper portion of the wicking, to allow analysis of a urine sample through contact of the urine with di assay strip; and wherein the urine wicks on the wicking solely in a direction from the base towards the opening of the container before contacting the assay strip.

* * * * *

UNITED STATES PATENT AND TRADEMARK OFFICE
CERTIFICATE OF CORRECTION

PATENT NO. : 6,805,837 B2
DATED : November 19, 2004
INVENTOR(S) : Barry M. Tydings It is certified that error appears in the above-identified patent and that said Letters Patent is hereby corrected as shown below:

Column 3,
Line 23, please delete the word "by" and replace with the word -- be -- to read, "urine sample need only be minimum in volume";

Column 4,
Line 11, please delete the word "other" to read, "ammonia, alcohol and sexually transmitted diseases";
Line 12, please delete the word "clomedia" and replace with the word -- Chlamydia -- to read "sexually transmitted diseases such as Chlamydia";

Column 8,
Line 29, please delete the word "contain" and replace with the word -- container -- to read, "the container and an upper portion proximal"; and
Line 34, please delete the word "di" and replace with the word -- the -- to read, "through contact of the urine with the assay strip".

Signed and Sealed this

Fifteenth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,805,837 B2 Page 1 of 1
DATED : October 19, 2004
INVENTOR(S) : Barry M. Tydings It is certified that error appears in the above-identified patent and that said Letters Patent is hereby corrected as shown below:

Title page,
Item [63], Related U.S. Application Data, replace with the following:
-- Continuation of application Ser. No. 10/091,162, filed Mar. 4, 2002 now U.S. Pat. No. 6,497,843, which is a Continuation of application Ser. No. 09/192,969, filed Nov. 16, 1998 now U.S. Pat. No. 6,379,620. --.

Column 1,
Line 5, after "6,497,843," insert -- which is a Continuation of application Ser. No. 09/192,969, filed Nov. 16, 1998 now U.S. Pat. No. 6,379,620. --.
Line 6, replace "which application" with -- The content of application Ser. No. 10/091,162, filed Mar. 4, 2002 now U.S. Pat. No. 6,497,843 --.

Signed and Sealed this

Twenty-ninth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,805,837 B2
DATED : October 19, 2004
INVENTOR(S) : Barry M. Tydings It is certified that error appears in the above-identified patent and that said Letters Patent is hereby corrected as shown below:

Title page,
Item [63], Related U.S. Application Data, replace with the following:
-- Continuation of application Ser. No. 10/091,162, filed Mar. 4, 2002 now U.S. Pat. No. 6,497,843, which is a Continuation of application Ser. No. 09/192,969, filed Nov. 16, 1998 now U.S. Pat. No. 6,379,620. --.

Column 1,
Line 5, after "6,497,843," insert -- which is a Continuation of application Ser. No. 09/192,969, filed Nov. 16, 1998 now U.S. Pat. No. 6,379,620. --.
Line 6, replace "which application" with -- The content of application Ser. No. 10/091,162, filed Mar. 4, 2002 now U.S. Pat. No. 6,497,843 --.

Signed and Sealed this

Third Day of January, 2006

JON W. DUDAS
*Director of the United States Patent and Trademark Office*

(12) EX PARTE REEXAMINATION CERTIFICATE (7381st)
United States Patent
Tydings

(10) Number: US 6,805,837 C1
(45) Certificate Issued: Feb. 23, 2010

(54) ASSAYING DEVICE AND METHOD FOR IN FIELD URINALYSIS

(75) Inventor: Barry M. Tydings, Westlake Village, CA (US)

(73) Assignee: Zyon Int'l Inc., Westlake Village, CA (US)

Reexamination Request:
No. 90/007,813, Nov. 23, 2005

Reexamination Certificate for:
Patent No.: 6,805,837
Issued: Oct. 19, 2004
Appl. No.: 10/264,605
Filed: Oct. 4, 2002

Certificate of Correction issued Feb. 15, 2005.

Certificate of Correction issued Nov. 29, 2005.

Certificate of Correction issued Jan. 3, 2006.

Related U.S. Application Data

(62) Division of application No. 10/091,162, filed on Mar. 4, 2002, now Pat. No. 6,497,843, which is a continuation of application No. 09/192,969, filed on Nov. 16, 1998, now Pat. No. 6,379,620.

(51) Int. Cl.
*G01N 33/558* (2006.01)

(52) U.S. Cl. .............................. 422/58; 422/50; 422/56; 422/60; 422/61; 422/102; 436/164; 436/169

(58) Field of Classification Search ........................ None
See application file for complete search history.

(56) References Cited

U.S. PATENT DOCUMENTS

| | | |
|---|---|---|
| 4,308,028 A | 12/1981 | Elkins |
| 4,599,219 A | 7/1986 | Cooper et al. |
| 4,883,641 A | 11/1989 | Wicks et al. |
| 5,004,584 A | 4/1991 | Rayman |
| 5,035,864 A | 7/1991 | Bell |
| 5,051,237 A | 9/1991 | Grenner et al. |
| 5,053,197 A | 10/1991 | Bowen |
| 5,104,812 A | 4/1992 | Kurn et al. |
| 5,110,727 A | 5/1992 | Oberhardt |
| 5,204,063 A | 4/1993 | Allen |
| 5,403,551 A | 4/1995 | Galloway et al. |
| 5,504,013 A | 4/1996 | Senior |
| 5,514,341 A | 5/1996 | Urata et al. |
| 5,547,833 A | 8/1996 | Dorval et al. |
| 5,607,863 A | 3/1997 | Chandler |
| 5,658,723 A | 8/1997 | Oberhardt |
| 5,668,017 A | 9/1997 | Buchanan et al. |
| 5,726,013 A | 3/1998 | Clark |
| 5,744,358 A | 4/1998 | Jackowski |
| 5,747,274 A | 5/1998 | Jackowski |
| 5,750,333 A | 5/1998 | Clark |
| 5,753,497 A | 5/1998 | Bernstein et al. |
| 5,756,362 A | 5/1998 | Durst et al. |
| 5,833,928 A | 11/1998 | Ratajczak et al. |
| 5,869,345 A | 2/1999 | Chandler |
| 5,871,700 A | 2/1999 | Konrad |
| 5,877,028 A | 3/1999 | Chandler et al. |
| 5,879,951 A | 3/1999 | Sy |
| 5,961,923 A | 10/1999 | Nova et al. |
| 5,998,220 A | 12/1999 | Chandler |

(Continued)

*Primary Examiner*—Jerry D. Johnson

(57) ABSTRACT

An assay device for in field urine analysis including a container having an opening for collecting a urine sample, a cover for sealing the opening of the container and an assay assembly provided in the container for chemically analyzing the urine sample. The assay assembly comprises a liquid impermeable backing, a wicking material provided on a rear surface of the backing, at least one assay strip provided on a front surface of the backing and adjacent a top edge of the backing in contact with the wicking material, a front cover provided on the front surface of the backing for sealing the assay strip to the backing at a bottom and two sides of the assay strip and a rear cover provided on the rear surface of the backing for together with the front cover sealing said wicking material and the assay strip adjacent the top edge and two sides of said wicking material.

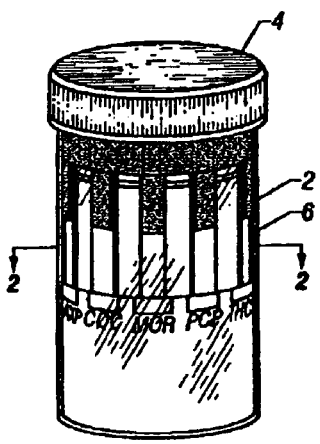

U.S. PATENT DOCUMENTS

| | | |
|---|---|---|
| 6,004,821 A | 12/1999 | Levine et al. |
| 6,017,496 A | 1/2000 | Nova et al. |
| 6,033,627 A | 3/2000 | Shields et al. |
| 6,040,195 A | 3/2000 | Carroll et al. |
| 6,046,057 A | 4/2000 | Nazareth et al. |
| 6,087,184 A | 7/2000 | Magginetti et al. |
| 6,106,779 A | 8/2000 | Buechler et al. |
| 6,156,272 A | 12/2000 | Lee et al. |
| 6,162,398 A | 12/2000 | Shuler |
| 6,197,494 B1 | 3/2001 | Oberhardt |
| 6,207,369 B1 | 3/2001 | Wohlstadter et al. |
| 6,214,629 B1 | 4/2001 | Freitag et al. |
| 6,248,596 B1 | 6/2001 | Durst et al. |
| 6,251,691 B1 | 6/2001 | Seul et al. |
| 6,287,783 B1 | 9/2001 | Maynard et al. |
| 6,316,205 B1 | 11/2001 | Guan et al. |
| 6,325,975 B1 | 12/2001 | Naka et al. |
| 6,328,931 B1 | 12/2001 | Silver et al. |
| 6,372,511 B1 | 4/2002 | Silver et al. |
| 6,375,897 B1 | 4/2002 | Bachand |
| 6,379,620 B1 | 4/2002 | Tydings et al. |
| 6,391,559 B1 | 5/2002 | Brown et al. |
| 6,406,922 B2 | 6/2002 | Casterlin et al. |
| 6,410,341 B1 | 6/2002 | Freitag et al. |
| 6,436,722 B1 | 8/2002 | Clark et al. |
| 6,451,619 B1 | 9/2002 | Catt et al. |
| 2002/0048819 A1 | 4/2002 | Alley |
| 2002/0085953 A1 | 7/2002 | Parker |
| 2002/0086436 A1 | 7/2002 | Buechler |
| 2002/0094301 A1 | 7/2002 | Tydings et al. |

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 4–6:

This application is a [Continuation] *Divisional* of application Ser. No. 10/091,162, filed Mar. 4, 2002, now U.S. Pat. No. 6,497,843, which is a Continuation of 09/192,969, filed Nov. 16, 1998 now U.S. Pat. No. 6,379,620. The content of application Ser. No. 10/091,162, filed Mar. 4, 2002 now U.S. Pat. No. 6,497,843 is incorporated herein by reference.

AS A RESULT OF REEXAMINATION, IT HAS BEEN DETERMINED THAT:

Claims 1–30 are cancelled.

* * * * *